United States Patent [19]

Schoeppel et al.

[11] Patent Number: 5,012,357
[45] Date of Patent: Apr. 30, 1991

[54] CT COMPATIBLE INTRACAVITY RADIATION APPLICATOR WITH AFTERLOADING SHIELDING

[75] Inventors: Sonja L. Schoeppel, Whitmore Lake, Mich.; Kenneth J. Weeks, Chapel Hill, N.C.; Kent R. Pruss, Ann Arbor, Mich.

[73] Assignee: University of Michigan, Ann Arbor, Mich.

[21] Appl. No.: 325,604

[22] Filed: Mar. 20, 1989

[51] Int. Cl.⁵ .............................................. A61N 5/10
[52] U.S. Cl. ........................................ 378/65; 378/20; 600/6; 600/7
[58] Field of Search ................. 600/3, 6, 7, 8; 378/65, 378/68, 205, 20

[56] References Cited

U.S. PATENT DOCUMENTS 3,807,386  4/1974  Rocoplan et al. ..................... 600/6

FOREIGN PATENT DOCUMENTS 0297350  4/1917  Fed. Rep. of Germany .......... 600/6

OTHER PUBLICATIONS

Haybittle et al., "A Simple After-Loading Technique for the Treatment of Cancer of the Cervix", *British Journal of Radiology*, vol. 48, No. 568, pp. 295-298, Apr. 1975.

*Primary Examiner*—Carolyn E. Fields
*Assistant Examiner*—David P. Porta
*Attorney, Agent, or Firm*—Rohm & Monsanto

[57] ABSTRACT

A system for providing therapeutic radiation to a predetermined tissue region within a body cavity of a living being utilizes an applicator arrangement which may, in a specific embodiment, comprise a pair of colpostats in conjunction with a tandem. The colpostats and tandem are formed of a material which is transparent to an imaging modality, such as CT scanning. Imaging-transparent source carriers containing dummy, or test, sources are placed in the colpostats. After the location of the colpostats, for example, has been determined, by imaging, the dummy source carriers are removed therefrom and replaced with selected source carriers containing actual radiation sources. The radiation source carriers further contain shielding which controls the strength and radiation pattern of the emitted radiation, all of which may be selected in response to the image. In a preferred embodiment, the dummy source carriers are provided with markings thereon which are opaque to imaging, so that the position and orientation of the source carriers with respect to the tissue region to be irradiated can be determined from the images. In an additional preferred embodiment wherein two colpostats are employed, certain ones of the source carriers are configured to be employed only with certain ones of the colpostats and/or visual markers are provided on the source carriers and the colpostats to avoid inadvertent misplacement.

18 Claims, 6 Drawing Sheets

CT COMPATIBLE INTRACAVITY RADIATION APPLICATOR WITH AFTERLOADING SHIELDING

BACKGROUND OF THE INVENTION

This invention relates generally to medical equipment systems of the type which apply therapeutic radiation to the internal tissues of the body of a living being following insertion of a source of radiation into a cavity within the body, and more particularly, to an applicator system which affords the facility to ascertain the suitability of a proposed location and position for a source of the therapeutic radiation within the body cavity prior to exposure of the living being to the radiation.

It is now well known to use hollow applicator tubes which contain radioactive sources for treatment of cancerous tissue, such as cancerous cervical tissue, within body cavities. In one early and widely used arrangement designed for the treatment by radiation of cervical cancer, hollow applicator tubes, or colpostats, are provided with radiation sources fixed therewithin. Metallic shields are provided for the purposes of directing the emission and shaping the field of exposure to the emitted radiation. It is a significant problem with this known arrangement that the patient's exposure to radiation commences immediately upon insertion of the applicator tubes, and prior to the adjustment of the location and position of the source, such that healthy tissue is disadvantageously exposed to the radiation.

Improvements to the early system permit emplacement of the hollow applicator tubes with the metallic shields attached thereto, and then afterloading of the radiation source into the applicator tubes. Such pre-placement of the hollow applicator tubes permits the user to predetermine, to a limited extent, the positioning of the applicator tube before the radiation source is inserted. Thus, the strength of the radiation capsule in each position may be chosen to optimize radiation dose. This arrangement includes the fixed metallic shields of the early system. The improved arrangement has attained significant acceptance, and is commercially available.

One drawback of the improved system is that when computerized tomography (CT) is used to scan the region to ensure proper placement of the applicator elements, the metallic shields cause CT image distortions called "streak artifacts." These distortions make discernment of the exact position of tissues adjacent to the applicator tubes very difficult.

It has been proposed to eliminate all metal shields on the applicator tube(s) and to use instead a non-metallic dummy (or test) source so as to obtain clear CT scan imaging of the tissues surrounding the placed applicator tubes, and when checking the pre-placement of the applicator ensemble in the vagina and uterus adjacent to the cervix. However, the prior art has not proposed a solution to the replacement of the removed exterior shielding. The prior art structure is not optimal because excessive radiation emission can adversely affect healthy tissues which may be in the vicinity of the applicator and which are not scheduled for irradiation.

Even when clear CT scans are made using a nominally CT-transparent test source, the applicator tubes may be seen to be properly located relative to the surrounding tissue, but it may be desirable to adjust the direction and emission pattern of the emitted radiation. Such adjustment, however, cannot be achieved using the known fixed shields. Even if the shields were adjustable, removal of the applicator tubes would be required, followed by reinsertion thereof and subsequent confirmation of location and position via further CT imaging. Thus, it would be desirable to be able to alter the shield geometry in response to the CT scan image, and to do so without requiring removal and reinsertion of the applicator tubes.

In addition to the foregoing, since more than one applicator tube and radiation source carrier are commonly used, it is very important that the proper radiation source carrier and applicator tube be paired to avoid error and incorrect treatment. This is especially critical since the usual practice is that the applicator tube placement and test imaging are performed in the hospital imager location, and the actual radiation source carriers may be inserted elsewhere, such as in the patient's room, since a long period of irradiation would otherwise encumber space in the operating clinic or test equipment areas.

It is, therefore, an object of this invention to provide a radiation applicator system which does not distort CT scan imaging.

It is another object of this invention to provide a radiation applicator system which does not distort CT scan imaging and which has adjustable shielding to attenuate radiation emitted by a contained radiation source.

It is additionally an object to provide a radiation applicator system having a combination of applicator tubes and radiation sources, with controllable shielding, wherein loading of a radiation source in a pre-placed applicator tube is facilitated, after the location of the applicator tube within the body cavity has been verified by imaging.

It is also an object of this invention to provide a radiation applicator system which permits alteration of the geometry of the shielding around the radiation source after the applicator tube(s) have been placed within the body and imaging of the region has been performed, to enable shaping of the field of exposure to the radiation and to ensure that a proper dose of radiation is administered to the selected tissue, while simultaneously blocking radiation emitted towards nearby non-selected tissue regions.

It is a further object of this invention to provide a radiation applicator system having applicator tubes which are fabricated from a material which does not degrade CT scanning and which can be manufactured sufficiently inexpensively so as to be disposable.

It is additionally an object of this invention to provide a radiation applicator system wherein a dummy source for standard x-ray simulation can be provided in addition to a dummy source which does not degrade CT images for CT scanning, to permit the resulting CT images to be of a quality sufficient to enable precise determination of the position of the actual radiation source vis-a-vis surrounding tissue structures.

Another object of the invention is to provide a radiation applicator system wherein CT images produced using a dummy source contain a visual indicator to assist in determining the exact position of the actual radiation source with respect to surrounding body tissues when the actual source replaces the dummy source.

It is yet a further object of this invention to provide a radiation applicator system having a combination of an applicator tube(s) together with a test or dummy source(s) which accurately represents the dimensions of the actual radiation source to be placed within the applicator tube, to facilitate placement of the radiation source within the body cavity and to provide clear test images, whereby proper placement and an estimate of the forthcoming radiation treatment efficacy can readily be ascertained.

It is also another object of this invention to provide a radiation applicator system constructed to have an applicator tube having a hollow portion having an inner diameter which accommodates a selectable one of either an actual radiation source, and appropriate shielding, or a dummy surrogate source which is used to predetermine the irradiation source location before final placement and treatment begins.

It is still another object of this invention to provide a radiation applicator system having multiple applicator tubes and means for identifying sets of applicator tubes and respective source carrier assemblies so that the proper radiation source and associated shields are inserted therein and inadvertent interchange of radioactive source carrier assemblies is prevented.

SUMMARY OF THE INVENTION

The foregoing and other objects are achieved by this invention which provides an arrangement for applying a therapeutic radiation emitted from a radiation source to a predetermined region of tissue within a cavity in the body of a living being. In accordance with the invention, the arrangement is provided with an applicator arrangement formed of a material transparent to a selected imaging modality, such as CT or x-ray. The applicator arrangement is provided with a hollow handle portion having an opening for obtaining access to the interior thereof, the opening being arranged at a first end of the applicator arrangement. The handle portion is coupled at a second end thereof to a hollow head portion which is arranged at a predetermined angle with respect to a longitudinal axis of the handle portion. A dummy source carrier is provided having a body which also is formed of imaging-transparent material, the dummy source carrier being provided with a central core formed of an imaging-transparent material. A bore is provided therein for accommodating a dummy substitute of the radiation source. In addition, a dummy source carrier handle is pivotally coupled to the dummy source carrier for facilitating insertion of the dummy source carrier through the opening of the hollow handle portion of the applicator arrangement and through to the hollow head portion thereof.

In accordance with a further aspect of the invention, a plurality of source carriers are provided. Each has a body provided with a central core having a bore therein for accommodating the radiation source, and a respectively associated shield affixed to the central core for blocking the radiation emitted by the radiation source. The shield has a predetermined configuration for achieving a desired predetermined radiation pattern. The particular one of the source carriers which is chosen for installation in the applicator, is selected in response to an image of the applicator with the dummy source carrier therein, within the body of the living being.

In a gynecologic applicator embodiment, the applicator arrangement consists of one or two colpostats (or applicator tubes) and a tandem. The colpostat has a hollow handle portion having an opening for obtaining access to the interior thereof, the opening being arranged at a first end of the colpostat. The handle portion is coupled at a second end thereof to a hollow head portion, which is arranged at a predetermined angle with respect to a longitudinal axis of the hollow handle portion. A source carrier for insertion into the colpostat has a body which is provided with a central core. The central core has a bore therein for accommodating a radiation source. In addition, the inventive source carrier is provided with a shield affixed to a surface of the central core for blocking radiation emitted by the radiation source. The shield has a predetermined configuration to produce a desired, predetermined radiation pattern from the radiation source. A source carrier handle is pivotally coupled to the source carrier for facilitating insertion of the source carrier through the opening of the hollow handle portion of the colpostat and urging same into the hollow head portion thereof.

In accordance with a specific embodiment of the invention, the source carrier is provided with an end cap for the central core which is formed of a radiation-blocking material. Preferably, the end cap has a sector thereof removed to permit a predetermined amount of the radiation to escape the source carrier in a desired pattern. Additionally, the source carrier is provided with an attachment cap, which also may be formed of a material transparent to imaging, for coupling pivotally to a source carrier handle.

A dummy source carrier is formed of a material transparent to imaging and configured in shape and size to be similar to the actual radiation source carrier. The dummy source carrier is used to permit imaging of the system, while it is inserted in the body of a patient in lieu of the radiation source carrier, without producing undesirable streaking artifacts in a CT image. Since the dummy source carrier would not be visible in the image, an identification marker which is opaque to the imaging system, which may be CT scanning, may be applied thereon in some embodiments to facilitate identification of the "dummy source" in CT imaging, as well as its position and orientation with respect to the tissue desired to be irradiated.

In a further embodiment of the invention, the hollow handle portion of the colpostat has a substantially cylindrical shape and the hollow head portion has a substantially cylindrical shape. In some embodiments, the hollow head portion may be ovoid-shaped. However, the shape of the hollow head portion, or the dummy and actual source carriers, may be cylindrical or any other shape desired. In this particular embodiment, the shape is configured to permit the colpostat head portions to encircle the cervix, and persons skilled in the art can design other shapes for different applications.

In a dual applicator tube embodiment of the invention, such as the gynecologic arrangement with tandem as described herein, one such applicator tube, or colpostat, may be configured to have a predetermined characteristic which differs from a corresponding characteristic of the other colpostat. In such an embodiment, the source carriers have respective characteristics which differ from one another, whereby each is adapted for insertion into a specific one of the colpostats. Such correspondence between the characteristics of the colpostats and the source carriers significantly reduces the possibility of inadvertent installation of an incorrect source carrier into a particular colpostat.

In a specific illustrative embodiment, the predetermined characteristic is a marker which provides a visual indication identifying the colpostats and the source carriers from one another. The visual marker may include a plurality of markings on respective ones of the source carrier handles and the handle portions of the colpostat.

In addition to the foregoing, the probability of error, such as cross-installation of the source carriers, may be reduced further by combining the aforementioned visual indication with a further predetermined identifying characteristic, such as respectively different handle lengths. By configuring the lengths of the source carrier handles to be different from each other, and to match with correspondingly different lengths of the colpostat handles, the possibility of improper installation of the radiation source is greatly reduced. For example, in the case of a long-handled source carrier inadvertently installed on a short-handled colpostat, the closure cap on the open end of the colpostat handle cannot be installed, thereby providing immediate indication of the error.

The applicator arrangement may also include a hollow tube with a curved end, commonly known as a tandem, for inserting into the uterine cavity. In the arrangement of the present invention, the tandem is fabricated from an imaging-transparent material. Actual radiation sources, or dummy sources, may be inserted into the tandem, as desired.

In accordance with a system aspect of the invention, a therapeutic radiation is applied to a predetermined tissue region within a cavity of the body of a living being, with the use of first and second applicators or colpostats. In some embodiments, a tandem, is used with the colpostats. The colpostats have respective handle portions, which may differ in length from one another, and respective head portions. As previously indicated, the first and second colpostats are formed of a material which is transparent to imaging, particularly imaging of the type which employs CT scanning.

The system is further provided with first and second source carriers, each containing a respective radiation source and a respective shield system, for emitting radiation in respective strengths and field patterns. Each such source carrier has associated therewith one of first and second source carrier handles which have different lengths and which may be pivotally coupled to the first and second source carriers, respectively. This facilitates insertion of the first source carrier into the first colpostat and the second source carrier into the second colpostat.

The first and second colpostat handles have associated therewith respective closure caps, each for closing an opening in a respective end of one of the colpostat handles after respective ones of the first and second source carriers have been installed therein. First and second dummy source carriers, formed of a material transparent to CT scanning, are provided for installing into the first and second colpostats prior to installation therein of the first and second radiation source carriers. In this manner, the location and position of the first and second source carriers within the body cavity can be determined prior to exposure of the living being to the radiation therefrom.

Further in accordance with the system aspect of the invention, the first and second dummy source carriers are configured in size and shape to correspond to the first and second source carriers. Moreover, there is further provided a marker for identifying the first and second dummy source carriers and the first and second colpostats, respectively.

In accordance with a method aspect of the invention, a method of applying a therapeutic radiation to a predetermined tissue region within a body cavity of a living being, includes the steps of inserting an applicator member into the body cavity of the living being; first installing in the applicator member a dummy source having dimensional characteristics corresponding to those of a radiation source; imaging the predetermined tissue region with the applicator member and dummy source in the body cavity, for forming an image which illustrates the location of the applicator member and the dummy source with respect to the predetermined tissue region; removing the dummy source from the applicator member; selecting a radiation source carrier with an appropriate radiation source and shields; and second installing the selected radiation source carrier in the applicator member for performing the radiation of the predetermined tissue.

The step of imaging is not limited to only one type of image, and may include several imaging modalities. For example, a first such image may be produced using x-ray technique, and a second image using CT. The x-ray image is less costly to produce, and more quickly obtained, affording certain information which may simplify, or otherwise facilitate, the CT imaging procedure.

In accordance with a specific method embodiment of the invention, the step of selecting includes the further step of comparing an identification marker on the applicator member with an identification marker associated with the source carrier. The step of inserting includes the further step of adjusting the position of radiation sources in a tandem which may be either free or coupled to the applicator member.

In a practical method aspect of the invention, there are provided the further steps of inserting a second applicator member into the body cavity of the living being substantially simultaneously with the applicator member; further installing in the second applicator member a second dummy source having dimensional characteristics corresponding to those of a further radiation source; removing the second dummy source from the second applicator member; selecting the further source carrier with a further radiation source and shields; and further installing the selected further source carrier in the second applicator member for irradiating the predetermined tissue. In order to minimize the risk of error, the method aspect of the invention contains the step of comparing an identification marker on the second applicator member with an identification marker associated with the further source carrier.

BRIEF DESCRIPTION OF THE DRAWING

Comprehension of the invention is facilitated by reading the following detailed description, in conjunction with the annexed drawing, in which.

DETAILED DESCRIPTION

Figure 1:
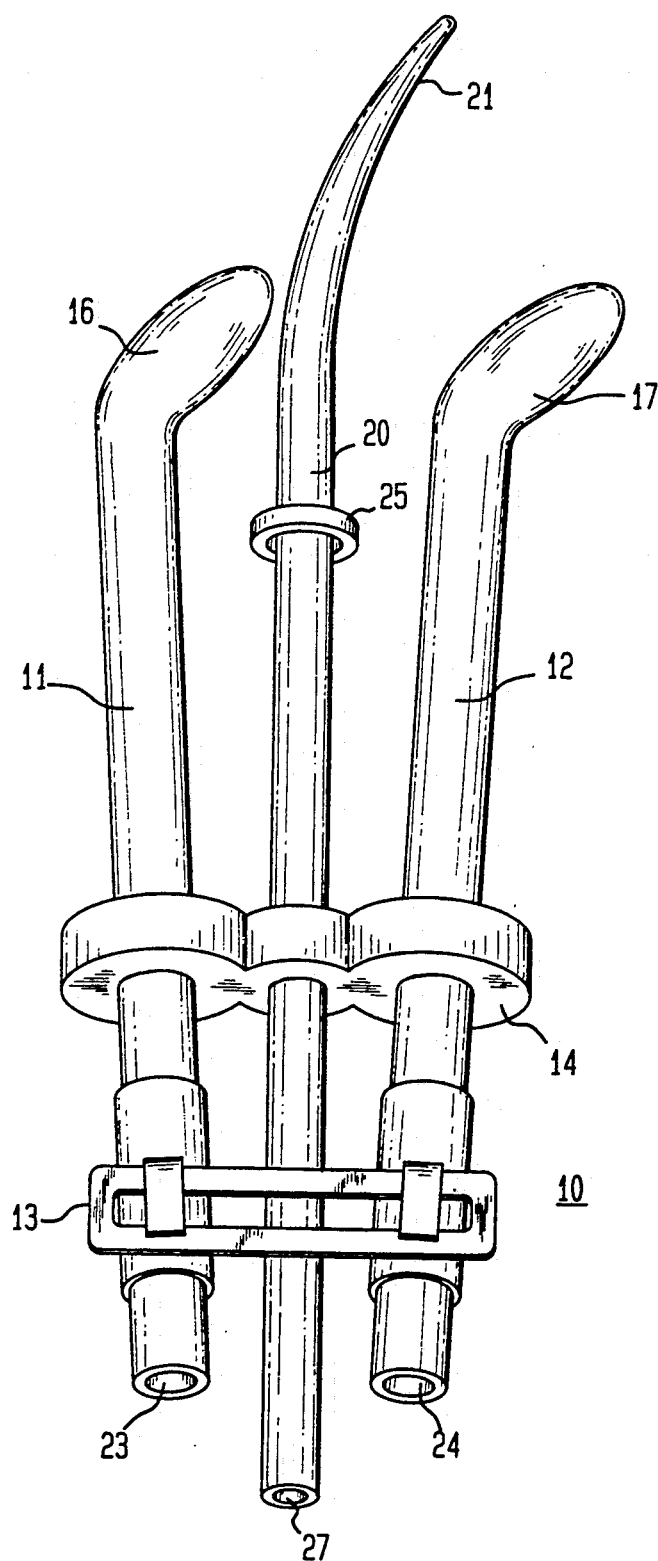
FIG. 1 is an isometric representation of a radiation applicator arrangement constructed in accordance with the invention for use in the region of the cervix.

FIG. 1 shows an applicator arrangement 10 which is to be placed during use in a body cavity (not shown) through an existing portal of the body of a living being. The specific illustrative embodiment shown herein is intended for placing an irradiation source adjacent to the cervix of a human being.

As shown in the Figure, applicator arrangement 10 comprises a colpostat 11 and a further colpostat 12 which are joined to one another by a pivot joint 13 near the base of each colpostat. In this embodiment, a yoke element 14 holds the various elements of applicator arrangement 10 together. In certain embodiments of the invention, a single colpostat, such as colpostat 11, may be used alone. It is, however, advantageous to employ two colpostats, linked as shown in the Figure, so as to permit two avenues for introducing irradiation sources (not shown in this Figure) within the body cavity. The specific illustrative embodiment of the present invention described herein provides each of colpostats 11 and 12 with respective ovoid-shaped head portions 16 and 17. Ovoid-shaped head portions 16 and 17 are configured fit in the lateral fornices and/or against the cervical portio. In a some embodiments, head portions 16 and 17 are cylindrical in shape. Such a cylindrical-shaped embodiment can be further provided with a sleeve (not shown) to increase the diameter of the head portion in order to compensate for anatomical differences between patients. In a practical embodiment cylindrical head portions 16 and 17 have a length of approximately 32 mm and a circumference of approximately 2 cm.

In the specific illustrative embodiment, applicator arrangement 10 is provided with an intrauterine tandem 20 which, in the embodiment shown in FIG. 1, is also secured in yoke 14. However, tandem 20 may float free of the other elements of applicator arrangement 10. Tandem 20 is positioned within the body cavity so that a tip portion 21 of tandem 20 just touches the upper end of the uterus (not shown). In a practical embodiment of the invention, intrauterine tandem 20 is formed of a CT-transparent material and has an outer diameter of some 8 mm. Flange 25 advantageously comprises CT-transparent plastic constructed around a CT-opaque angiocath segment so that flange 25 is visible on the CT scan and marks the location of the external cervical os. Flange 25 also prevents the tandem from perforating the uterine wall. Tandem 20 can also be adapted to carry a selectable one of a dummy source or radiation source, inserted through opening 27.

The hollow handle portions of colpostats 11 and 12 are open at the base, permitting insertion therethrough of selectable ones of radiation and test (dummy) sources (not shown in this Figure). The distal ends of the colpostats, as previously noted, are closed by ovoid-shaped head portions 16 and 17 which are arranged at predetermined angles with respect to the central longitudinal axes (not shown) of their respective handle portions. In this specific embodiment, the angle is approximately 75°. The ovoid-shaped head portions will house the dummy or irradiation sources, as will be described hereinbelow.

In a practical embodiment, a colpostat is formed in symmetrical halves of milled acrylic plate having a 9.5 mm thickness. The two halves may be bonded together, illustratively using a solvent, and machined to produce a cylinder having a diameter sufficient to accommodate the source carrier assemblies described hereinbelow. In a practical embodiment, the diameter of the colpostat is on the order of 20 mm.

Figure 2:
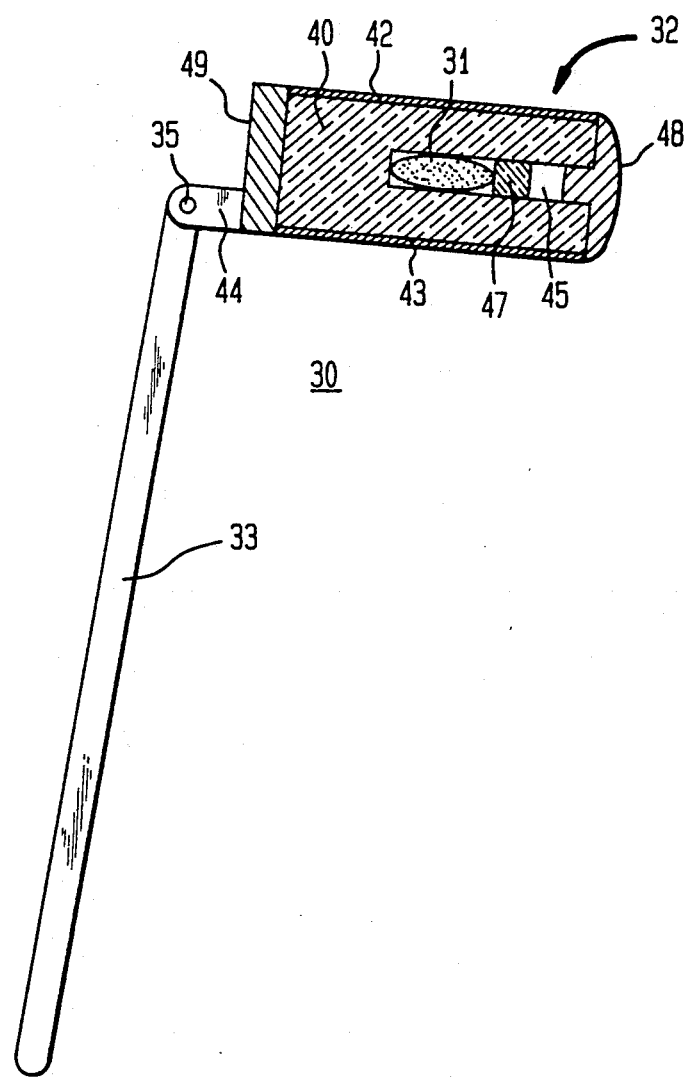
FIG. 2 is a partially cross-sectioned plan view of a treatment insertion assembly with radiation source and shields in place.

FIG. 2 shows a partially cross-sectioned plan view of a treatment insertion assembly 30. The treatment insertion assembly comprises a radiation source 31 which is installed in a source carrier 32 which is attached to an insertion rod or handle 33 by a flexible joint 35.

Treatment insertion assembly 30 is designed to be placed within one of bore 23 and bore 24 of colpostat 11 and colpostat 12, respectively, shown in FIG. 1. Treatment insertion assembly 30 is urged through the selected one of bores 23 and 24 until source carrier 32 is disposed in the selected one of hollow head portions 16 and 17. Flexible joint 35 allows angulation of treatment insertion assembly 30 during its traverse through the bore, thereby facilitating entry of source carrier 32 into an angulated ovoid end. Although the embodiment of FIG. 2 shows handle portion 33 to be a straight rod, the rod may be slightly bent to facilitate passage of the source carrier through the bore and into the head portion.

FIG. 2 presents a cross-sectional representation of source carrier 32 showing the structure therewithin. The interior portion of source carrier 32 is provided with a central core 40 formed of an imaging-transparent material such as Lucite plastic (a trademark of E.I. Dupont de Nemours & Co., Wilmington, Delaware) which is easily machined and is suitable for containing radiation source 31, which may be formed of a radioactive material such as radium or cesium-137. Of course, interior core 40 could be formed by a molding process rather than machining.

Source carrier 32 is provided with a shielding arrangement comprising upper shield 42 and lower shield 43. The function of the shielding arrangement is to control the pattern of emitted radiation from radiation source 31 which is housed within source carrier 32. The specific pattern of emitted radiation is selected to achieve the goal of properly irradiating the target tissue in the body cavity, such as cervical tissue, while limiting the radiation that is applied to other nearby tissues, such as rectal and bladder tissues.

Upper shield member 42 is constructed of a material which attenuates the radiation from radiation source 31, such as a tungsten alloy (90% tungsten, 6% nickel, 4% copper, with a density illustratively on the order of 17 $gm/cm^3$). Upper shield member 42 can be affixed, such as with the use of a fast-setting epoxy resin adhesive, to an outer surface of central core 40. Lower shield member 43 may be affixed in a similar manner to central core 40. In a further embodiment of the invention, source carrier 32 may have a fixed shell housing (for example, stainless steel tubing) with a shielding arrangement affixed thereto.

As can be seen from FIG. 2, radiation source 31 is disposed in an axial bore 45 which is drilled through the center of central core 40. After radiation source 31 is installed within axial bore 45, the source may be secured in place, illustratively by a plug 47 also formed of Lucite plastic. In this specific illustrative embodiment, an end cap 48 is installed on one end of central core 40 so as to provide a closed, rounded frontal end for source carrier 32, thereby facilitating its traverse along bore 23 or bore 24 of the colpostats of FIG. 1. Additionally, the somewhat rounded frontal end facilitates angulation and entry into ovoid-shaped head portions 16 and 17.

Source carrier 32 is completed by the addition of an attachment end cap 49 which is affixed to central core 40 at an end distal to end cap 48. The total length of source carrier 32 is on the order of 30 mm, specifically 32 mm in a practical embodiment. Additionally, attachment end cap 49 is provided with a lug 44 which is coupled to insertion rod 33 by means of flexible joint 35, which may be a pin joint.

In a particularly advantageous embodiment of the invention, the components of treatment insertion assembly 30 are constructed from an imaging-transparent material. Of course, certain elements of the source carrier 32, such as shields 42 and 43 and the radiation source 31 would be visible to an imaging modality. However, test imaging is accomplished with a test insertion assembly, to be described hereinbelow, installed in the colpostats. Thus, the treatment insertion assembly components could also comprise a metallic material, such as stainless steel.

Figure 3:
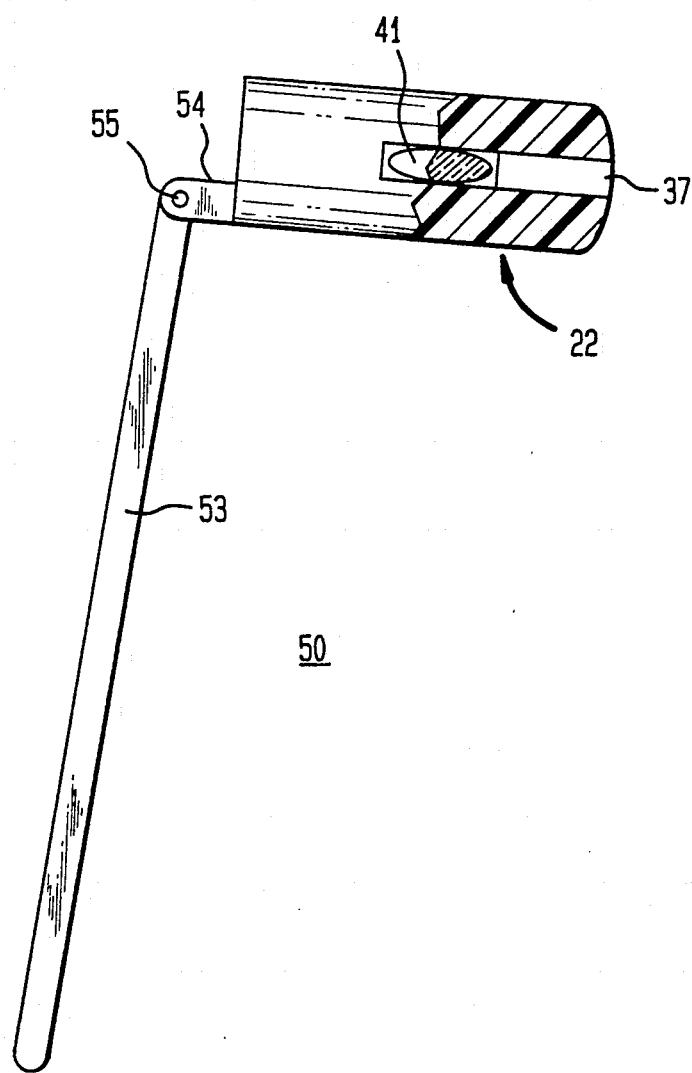
FIG. 3 is a partially cross-sectioned plan view of a test insertion assembly with a dummy source in place.

FIG. 3 shows a partially cross-sectioned plan view of a test insertion assembly 50 which is specifically adapted to carry a dummy (or test) source 41. Test insertion assembly 50 comprises a dummy source carrier 22 which is made of a material which can easily be configured to the same overall shape and size of the radiation source carrier. Dummy source carrier is provided with a lug 54 which is coupled to insertion rod 53 by means of flexible joint 55. Additionally, dummy source carrier 22 is fabricated from a material, such as an acrylic polymer, which is substantially imaging-transparent. Dummy source carrier 22 has a bore 37 therethrough into which a dummy source 41 is inserted. In one embodiment, dummy source 41 is adapted for x-ray simulation and comprises a stainless steel pellet of substantially the same size and configuration as an actual radiation source. In alternate embodiments, dummy source 41 comprises a CT-opaque angiocath segment of length equivalent to an actual radiation source and is particularly adapted for CT scan imaging.

Figure 4:
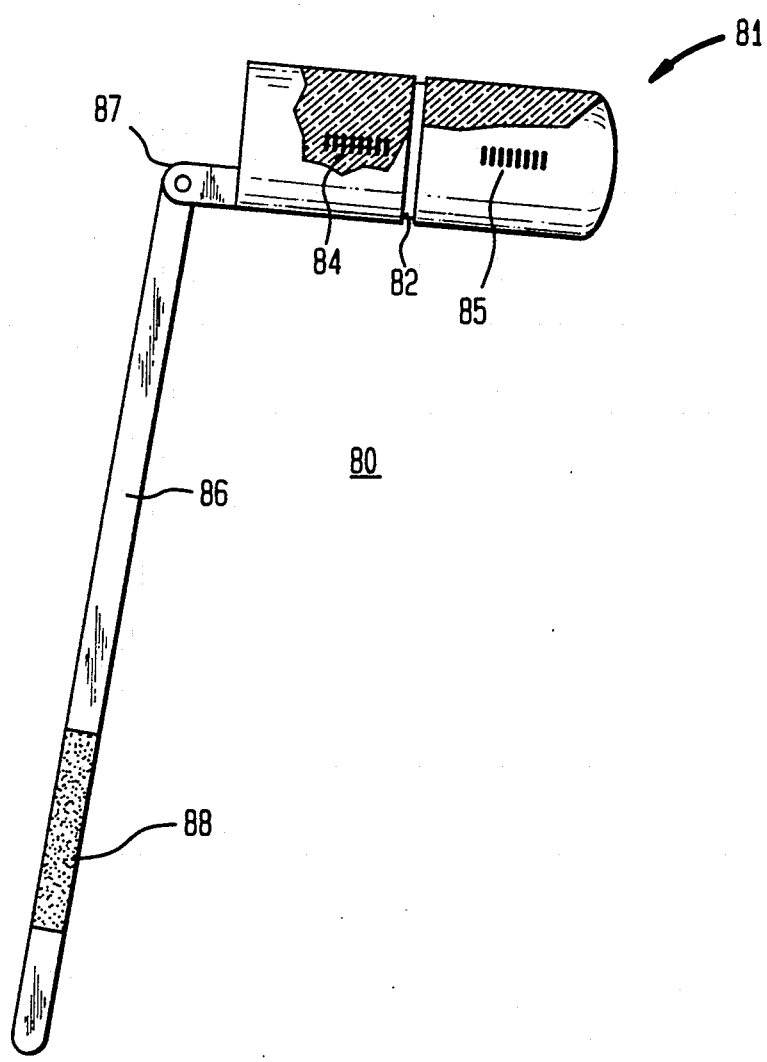
FIG. 4 is partially fragmented view of an alternative embodiment of a test insertion assembly.

FIG. 4 is a partially fragmented view of another embodiment of a test insertion assembly 80. In this aspect of the invention, the radioactive source carrier is replaced by a dummy source carrier 81 wherein the position of dummy source carrier 81 is made clearly visible on the test CT screen, for example, by a marker band 82 which may be placed around the central circumference of dummy source carrier 81 and marker strips 84 and 85 may be placed on a surface of test capsule 81 in alignment with the axis of the cylinder at intervals such as is shown in FIG. 4. Marker band 82 and marker strips 84 and 85 comprise a thin material strip substantially opaque to CT scanning. The dummy source carrier 81 is attached to an insertion rod 86 at a flexible joint 87. An imaging-opaque strip 88 may also be placed along insertion rod 86 to aid localization on the CT scan image. In a preferred embodiment, insertion handle 86 is fabricated from the same acrylic plastic as dummy source carrier 81 so that the entire test insertion assembly has little metallic mass, thereby avoiding the production of streaking artifacts during CT scanning. In this manner, the CT scan of the region will be clear and the position of test insertion assembly 80 and dummy source carrier 81 can accurately be measured in relationship to the nearby tissues of the body. This will enable determination of the probable efficacy of the radiation treatment when the radioactive source carrier is used in place of the dummy source carrier.

Figure 5:
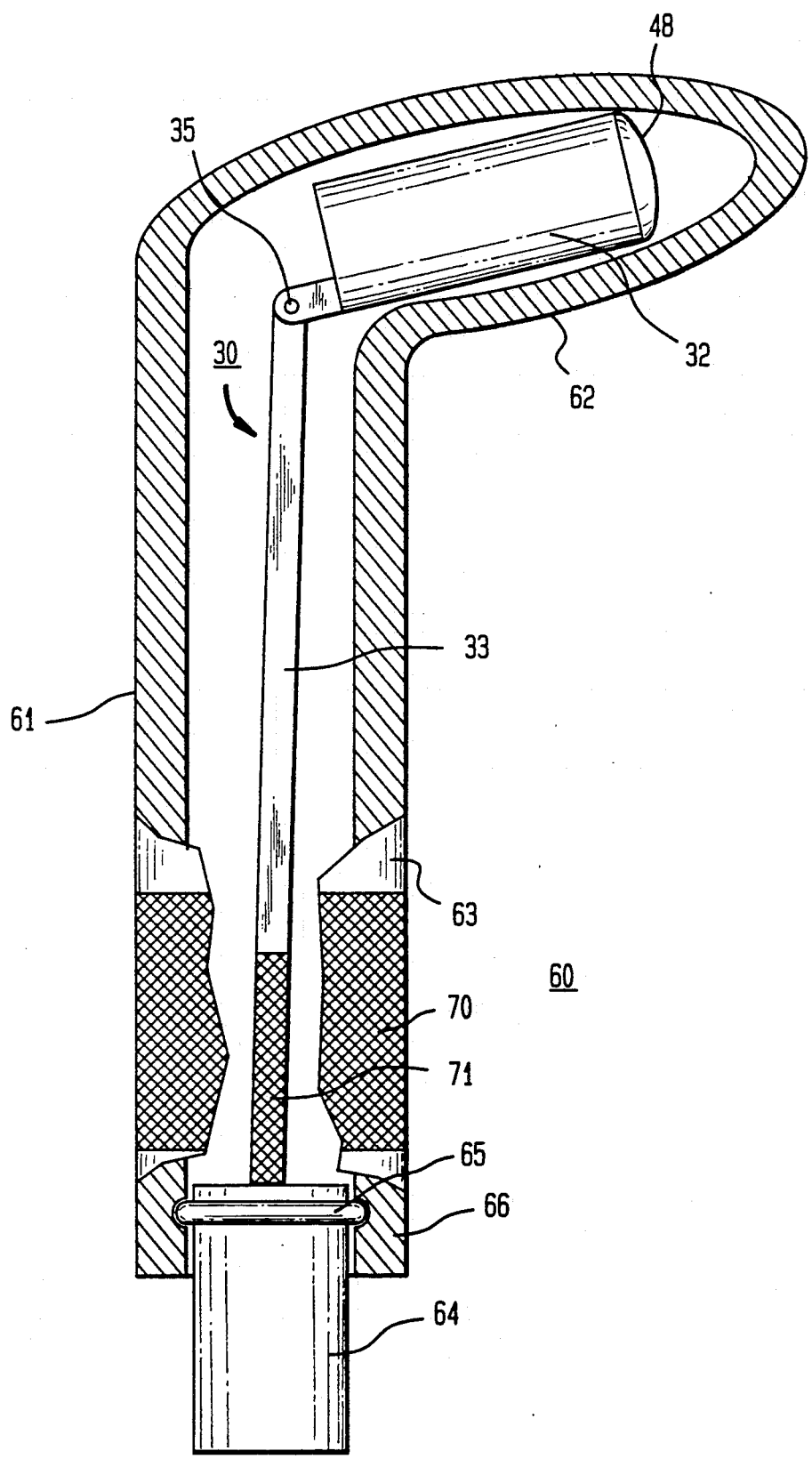
FIG. 5 is a partially cross-sectioned plan view of an applicator tube ensemble, specifically a colpostat ensemble in this embodiment, showing an insertion assembly therein.

FIG. 5 is a partially cross-sectioned representation of an applicator tube (colpostat) ensemble 60 comprising a colpostat 63 having a handle portion 61 and a head portion 62. As shown, applicator tube ensemble 60 contains an insertion assembly, which in this Figure, is treatment insertion assembly 30 described herein with respect to FIG. 2. The insertion assembly is shown to be inserted fully into ovoid-shaped head portion 62. Test insertion assembly 20, described herein with respect to FIG. 3, would be installed into colpostat 63 in the same manner.

In situations where two colpostats are utilized in patient treatment, such as applicator arrangement 10 described with respect to FIG. 1, each such colpostat may be adapted specifically for use with only one of two insertion assemblies. This specificity of use may be provided by specifying the length of handle portion 61 and insertion rod 33 of insertion assembly 30. Illustratively, insertion assemblies can be provided wherein the corresponding parts have lengths which differ by 6 mm. Thus, if the source carrier assembly which has the 6 mm longer insertion rod were to be placed inadvertently in the colpostat having the shorter length to the ovoid head, the lower end of the insertion rod would protrude from the opening of the colpostat bore. Such protrusion would prevent proper seating of a bore closure cap 64, whereby a locking tongue ring 65 would not properly engage an annular groove 66 in the wall of colpostat 63.

In addition to the foregoing, a color coding system may be used to facilitate identification of associated insertion assemblies and colpostats. Such color coding is readily achieved in accordance with the invention by providing a distinctive color code illustratively on a colpostat color code band 70 on handle portion 61 of colpostat 63, as shown in FIG. 5. Insertion rod 33 bears an identical color code on rod color code band 71.

FIG. 5 shows colpostat 63 with the treatment insertion assembly 30 installed therein. However, prior to insertion of a radioactive source, a standard x-ray simulation is performed using a stainless steel dummy source in the test insertion assembly of FIG. 3. In embodiments where a tandem is used, a dummy source would also be installed in the tandem. Following x-ray simulation, the stainless steel dummy sources are removed and replaced with CT-opaque angiocath segments as discussed hereinabove. A CT scan allows detailed visualization of the relationship of various tissue structures and the applicator arrangement elements which may not be revealed by the simulation radiographs. Moreover, the ability to perform CT scans of diagnostic quality with the applicator in place allows full three-dimensional treatment planning with a three-dimensional solid surface graphic display as well as dose volume histogram analysis. The graphic display is particularly helpful in visualizing the relationship of the treatment isodose volume to the structures of interest. Using dose volume histogram data, the maximum and minimum dose to the cervix, rectum, and bladder can be precisely identified along with the volume of tissue receiving the dose.

Advantageously, the arrangement herein allows for both shielding and unimpaired CT images since the shielding arrangement is after-loaded along with the radiation source. A further significant advantage is that individualized shielding can be devised to optimize protection of the bladder and rectum without compromising the dose to the tumor. Moreover, such customized shielding could compensate for anatomic and applicator placement variations.

Figure 6:
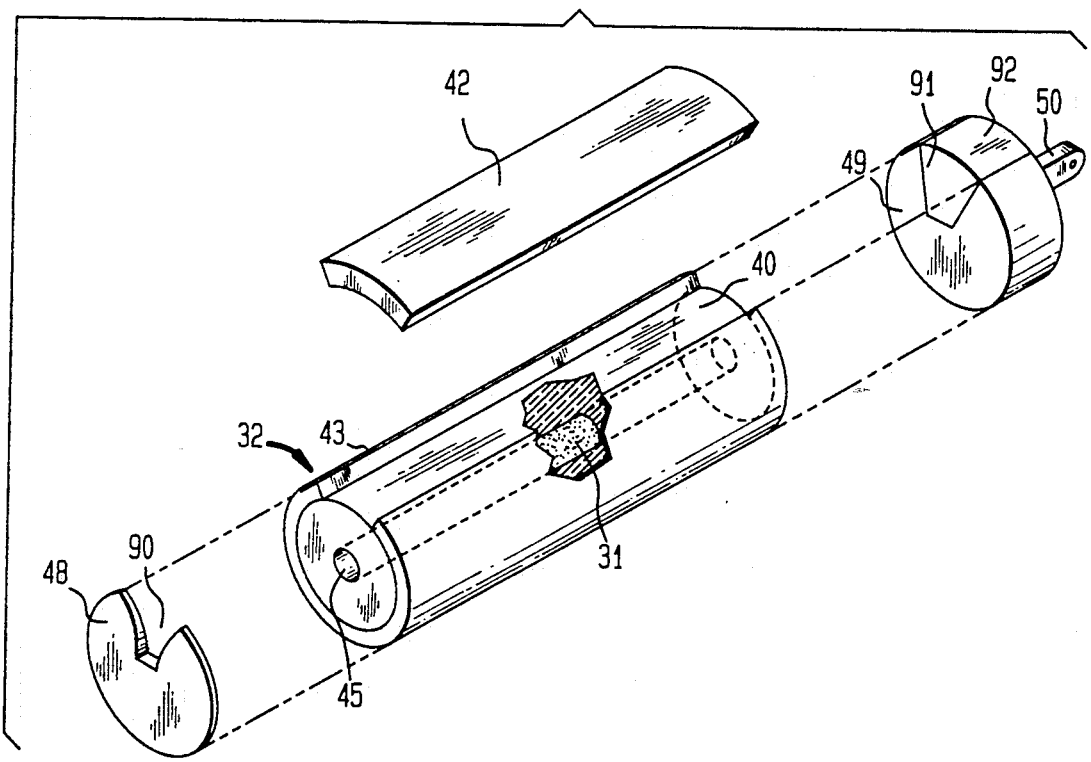
FIG. 6 is an exploded isometric representation of a specific illustrative embodiment of a radiation source carrier.

Referring to FIG. 6, an exploded isometric representation of the shielding arrangement of source carrier 32 is shown. Once the proximity of nearby body tissues is determined from x-ray simulation and/or the test CT scan made with a dummy source carrier, a desirable pattern of emission from actual radiation source 31, can be chosen to ensure optimal radiation dosage to the selected tissues, and to minimize the risk of exposure of the healthy tissue. In a specific illustrative embodiment, the emitted radiation pattern is configured by fabricating upper shield 42 and lower shield 43 to surround radiation source 31 in a selectable pattern. When shields 42 and 43 are affixed to central core 40, their selective exposure and masking of radiation source 31 will determine the strength and pattern of the radiation emission which escapes to the tissues within the body cavity.

End cap 48 and attachment end cap 49 can also be fabricated from a radiation-blocking material, such as tungsten alloy. End cap 48 can expose the source over a chosen area by cutting a sector notch 90. Moreover, attachment end cap 49 is provided with a sector notch 91 having a selectable configuration. Weakening of attachment end cap 49 as a result of cutting away material is minimized by providing sector cover 92 affixed in the notch. Sector cover 92 preferably is made of a radiation transparent material such as Lucite plastic. If desired, end cap 48 can be left unattached to central core 40 so that radiation source 31 can be loaded into axial bore 45 just prior to treatment of the patient, and after upper shield 42 and lower shield 43 have been affixed to the central core.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. An arrangement for applying a therapeutic radiation emitted from a radiation source to a predetermined region of tissue within a cavity in the body of a living being, the arrangement comprising:

applicator means formed of an imaging-transparent material and having a hollow handle portion having an opening for obtaining access to the interior thereof, said opening being arranged at a first end of said applicator means, and being coupled at a second end thereof to a hollow head portion, said hollow head portion being arranged at a predetermined angle with respect to a longitudinal axis of said hollow handle portion;

dummy source carrier means having a body formed of imaging-transparent material, said dummy source carrier means being provided with dummy central core means formed on an imaging-transparent material and having a bore therein for accommodating a dummy substitute of the radiation source;

dummy source carrier handle means pivotally coupled to said dummy source carrier means for facilitating insertion of said dummy source carrier means through said opening of said hollow handle portion of said applicator means and through to said hollow head portion thereof; and source carrier means having a body provided with a central core means having a bore therein for accommodating the radiation source, and a respectively associated shield means affixed to said central core means for blocking the radiation emitted by the radiation source, said shield means having a predetermined configuration which corresponds to a predetermined radiation pattern.

2. The arrangement of claim 1 wherein said hollow handle portion has a substantially cylindrical shape and said hollow head portion also has a substantially cylindrical shape.

3. The arrangement of claim 1 wherein there are provided a plurality of said source carrier means, each being selectable for installation in said applicator means in response to an image of said applicator means with said dummy source carrier means therein within the body of the living being.

4. The arrangement of claim 3 wherein said dummy source carrier means is further provided with identification marker means opaque to imaging for facilitating identification of said dummy source carrier means in said image.

5. The arrangement of claim 1 wherein there is further provided source carrier handle means pivotally coupled to said source carrier means for facilitating insertion of said source carrier means through said opening of said hollow handle portion of said applicator means and through to said hollow head portion thereof.

6. The arrangement of claim 5 wherein there is further provided visual marker means for providing a visual indication identifying at least one of said source carrier means.

7. The arrangement of claim 6 wherein said visual marker means comprises a further marking disposed on said source carrier handle means.

8. The arrangement of claim 5 wherein there is further provided attachment cap means formed of a radiation blocking material and for coupling pivotally to said source carrier handle means.

9. The arrangement of claim 1 wherein there is further provided end cap means formed of a radiation blocking material, said end cap means having a sector thereof removed to permit a predetermined amount of the radiation to escape said source carrier means.

10. The arrangement of claim 1 wherein said dummy source carrier means is configures in shape and size to be similar to at least a one of said source carrier means.

11. The arrangement of claim 5 wherein the lengths of said plurality of source carrier handle means differ from one another and correspond to correspondingly different lengths of said applicator means.

12. A system for applying therapeutic radiation to a predetermined tissue region within a cavity of the body of a living being, the system comprising:

first and second colpostat means, each having a respective handle portion and a respective head portion, said first and second colpostat means being formed of a material which is transparent to CT scanning;

first and second source carrier means, each containing a respective radiation source and having a respectively associated shield arrangement, for controlling emission of radiation in respective strengths and field patterns;

first and second source carrier handle means each being pivotally coupled to an associated one of said first and second source carrier means for facilitating insertion of said first source carrier means with its associated shield arrangement into said first colpostat means, and said second source carrier means with its associated shield arrangement into said second colpostat means, respectively; and first and second handle closure means each for closing an opening in a respective one of said handle portions after respective ones of said first and second source carrier means have been installed in said colpostat means.

13. The system of claim 12 wherein there are further provided first and second dummy source carrier means formed of a material transparent to CT scanning, for installing into said first and second colpostat means prior to installation therein of said first and second source carrier means and associated shield arrangements, and for determining a location and position of said first and second colpostat means within the body cavity prior to exposure of the living being to radiation from the radiation sources.

14. The system of claim 12 wherein there is further provided tandem means.

15. A method of applying a therapeutic radiation to a predetermined tissue region within a body cavity of a living being, the method comprising the steps of:
    inserting an applicator member into the body cavity of the living being, said applicator member being formed of a material transparent to imaging;
    first installing in said applicator member a dummy source carrier;
    imaging the predetermined tissue region with said applicator member and said dummy source carrier in the body cavity, for forming an image which illustrates the location of said applicator member and said dummy source carrier with respect to the predetermined tissue region;
    removing said dummy source carrier from said applicator member;
    selecting a source carrier with a radiation source therein having a predetermined dose and a respectively associated shielding having a predetermined shielding pattern, in response to said image formed in said step of imaging; and
    second installing said selected source carrier with said radiation source and said associated shielding in said applicator member for performing the radiation of the predetermined tissue.

16. The method of claim 15 wherein said step of selecting comprises the further step of comparing an identification marker on said applicator member with an identification marker associated with said source carrier.

17. The method of claim 15 wherein there are provided the further steps of:
    inserting a second applicator member into the body cavity of the living being substantially simultaneously with said applicator member;
    further installing in said second applicator member a second dummy source carrier;
    removing said second dummy source carrier from said second applicator member;
    selecting a further source carrier with a further radiation source therein and a further shield; and
    further installing said selected further source carrier in said second applicator member for performing the radiation of the predetermined tissue.

18. The method of claim 17 wherein said step of selecting a further source carrier comprises the further step of comparing an identification marker on said second applicator member with an identification marker associated with said further source carrier.

* * * * *